United States Patent [19]
Slotman et al.

[11] Patent Number: 5,599,279
[45] Date of Patent: Feb. 4, 1997

[54] SURGICAL INSTRUMENTS AND METHOD USEFUL FOR ENDOSCOPIC SPINAL PROCEDURES

[75] Inventors: Gus J. Slotman, 705 Mill St., Moorestown, N.J. 08057; Sherman Stein, 310 Spruce St., Philadelphia, Pa. 19106; David T. Green, Westport, Conn.; Salvatore Castro, Seymour, Conn.; Carlo A. Mililli, Huntington, Conn.; Keith Ratcliff, Sandy Hook, Conn.

[73] Assignees: Gus J. Slotman; Sherman Stein; United States Surgical Corporation, all of Norwalk, Conn.

[21] Appl. No.: 593,191

[22] Filed: Jan. 29, 1996

Related U.S. Application Data

[63] Continuation of Ser. No. 214,875, Mar. 16, 1994, abandoned.

[51] Int. Cl.$^6$ ..................................................... A61B 17/00
[52] U.S. Cl. ........................ 600/201; 128/878; 600/235
[58] Field of Search .................. 128/898, 20; 606/61, 606/130, 198; 600/201, 210, 217, 219, 235

[56] References Cited

U.S. PATENT DOCUMENTS

| | | |
|---|---|---|
| Re. 33,258 | 7/1990 | Onik et al. . |
| 832,201 | 10/1906 | Kistler . |
| 1,331,737 | 2/1920 | Ylisto . |
| 1,400,648 | 12/1921 | Whitney . |
| 1,737,488 | 11/1929 | Zohlen . |
| 2,067,031 | 1/1937 | Wappler . |
| 2,137,121 | 11/1938 | Greenwald . |
| 2,689,568 | 9/1954 | Wakefield . |
| 3,486,505 | 12/1969 | Morrison . |
| 3,916,907 | 11/1975 | Peterson . |
| 4,034,746 | 7/1977 | Williams . |
| 4,174,715 | 11/1979 | Hasson . |
| 4,369,788 | 1/1983 | Goald . |
| 4,393,872 | 7/1983 | Reznik et al. . |
| 4,545,374 | 10/1985 | Jacobson . |
| 4,573,448 | 3/1986 | Kambin . |
| 4,599,086 | 7/1986 | Doty . |
| 4,654,028 | 3/1987 | Suma . |
| 4,655,219 | 4/1987 | Petruzzi . |
| 4,747,394 | 5/1988 | Watanabe . |
| 4,896,661 | 1/1990 | Bogert et al. . |
| 4,898,161 | 2/1990 | Grundei . |
| 4,909,789 | 3/1990 | Taguchi et al. . |
| 4,926,849 | 5/1990 | Downey . |
| 4,932,395 | 6/1990 | Mehdizadeh . |
| 4,997,432 | 5/1991 | Keller . |
| 5,000,163 | 3/1991 | Ray et al. . |
| 5,019,081 | 5/1991 | Watanabe . |
| 5,027,793 | 7/1991 | Engelhardt et al. . |
| 5,113,846 | 5/1992 | Hilterbrandt et al. . |
| 5,122,130 | 6/1992 | Keller . |
| 5,152,279 | 10/1992 | Wilk . |
| 5,176,129 | 1/1993 | Smith . |
| 5,178,133 | 1/1993 | Pena . |
| 5,195,506 | 3/1993 | Hulfish . |
| 5,195,507 | 3/1993 | Bilweis . |

(List continued on next page.)

FOREIGN PATENT DOCUMENTS

| | | |
|---|---|---|
| 77159 | 4/1983 | European Pat. Off. . |
| 260044 | 3/1988 | European Pat. Off. . |
| 8303342 | 7/1983 | Germany . |
| WO93/17625 | 9/1993 | WIPO . |

*Primary Examiner*—Richard J. Apley
*Assistant Examiner*—Beverly M. Flanagan

[57] ABSTRACT

The present invention provides endoscopic instrumentation and surgical techniques especially useful for accessing at least a portion of an intervertebral disc. Vertebrae spreading instruments are provided for spreading adjacent vertebrae to facilitate access to the intervertebral disc are. The disclosed surgical method uses an anterior approach to access the intervertebral disc and spreads adjacent vertebrae utilizing an endoscopic vertebrae spreading instrument.

12 Claims, 8 Drawing Sheets

U.S. PATENT DOCUMENTS

| | | | |
|---|---|---|---|
| 5,195,541 | 3/1993 | Obenchain | 128/898 |
| 5,197,971 | 3/1993 | Bonutti . | |
| 5,213,112 | 5/1993 | Niwa et al. . | |
| 5,235,966 | 8/1993 | Jamner . | |
| 5,241,972 | 9/1993 | Bonati | 128/898 |
| 5,242,439 | 9/1993 | Larsen et al. . | |
| 5,275,610 | 1/1994 | Eberbach . | |
| 5,313,962 | 5/1994 | Obenchain . | |
| 5,357,983 | 10/1994 | Mathews . | |
| 5,439,464 | 8/1995 | Shapiro . | |

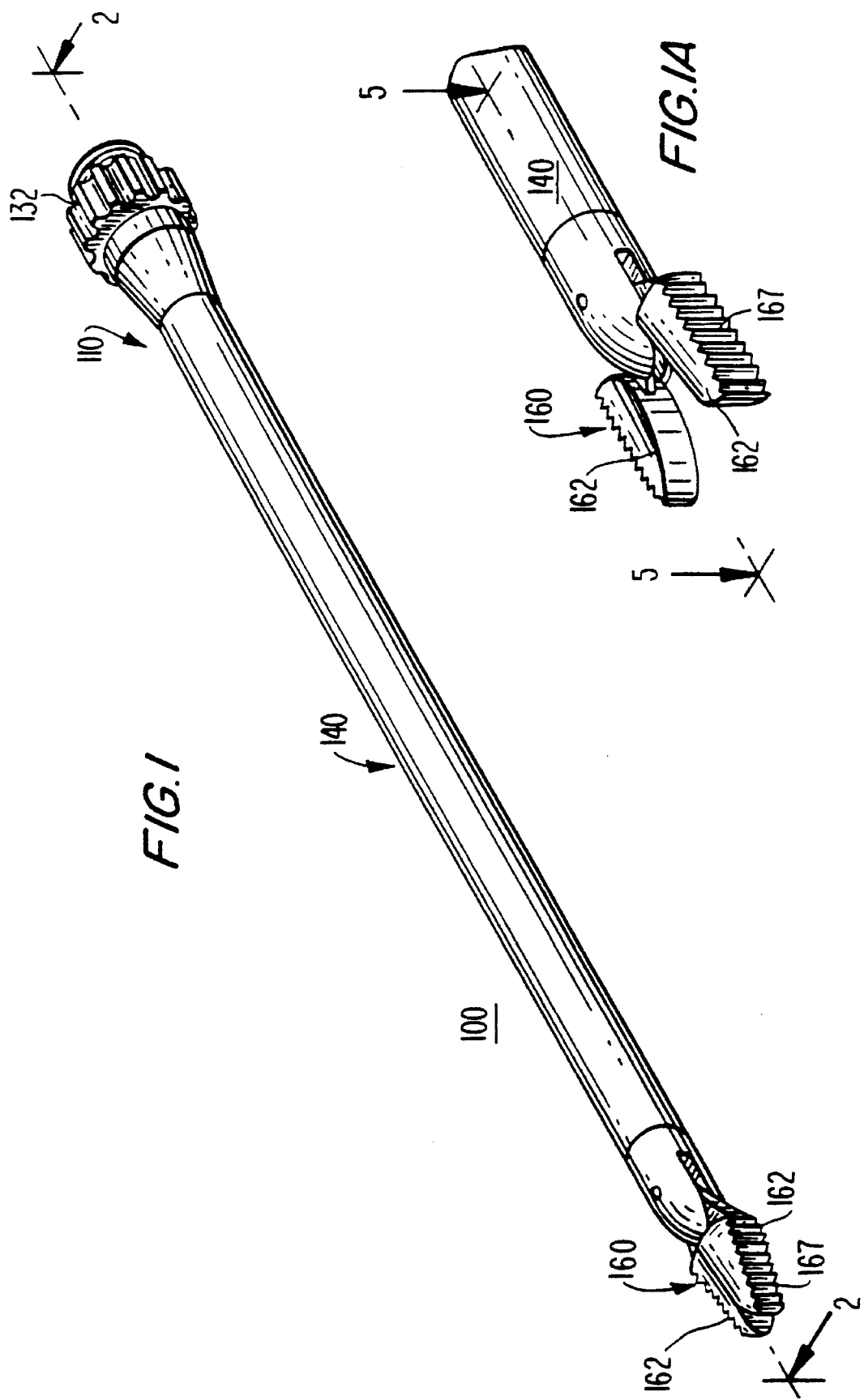

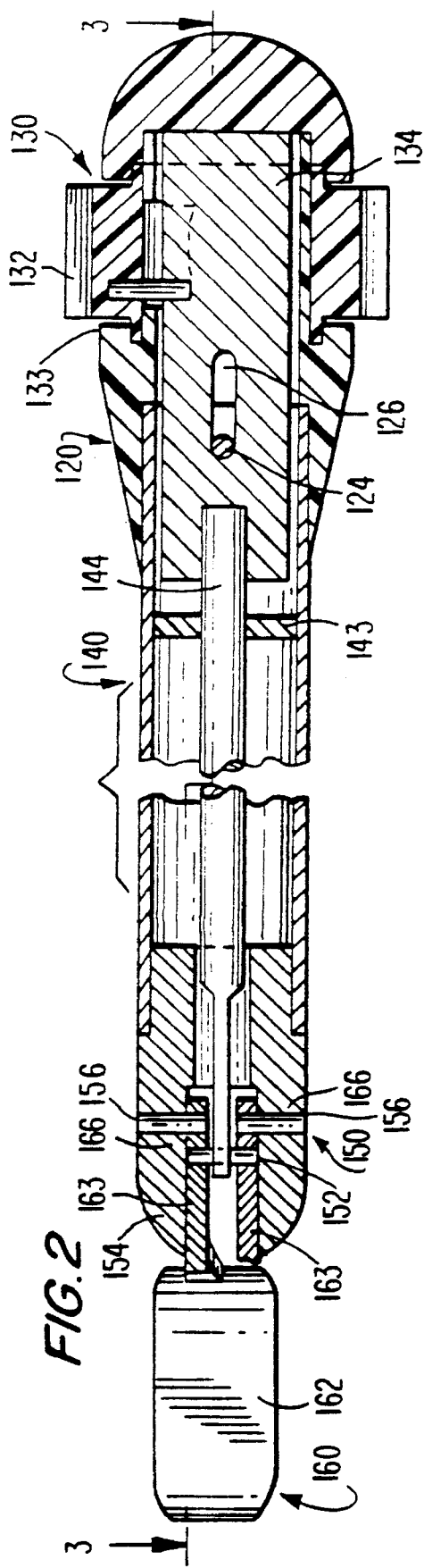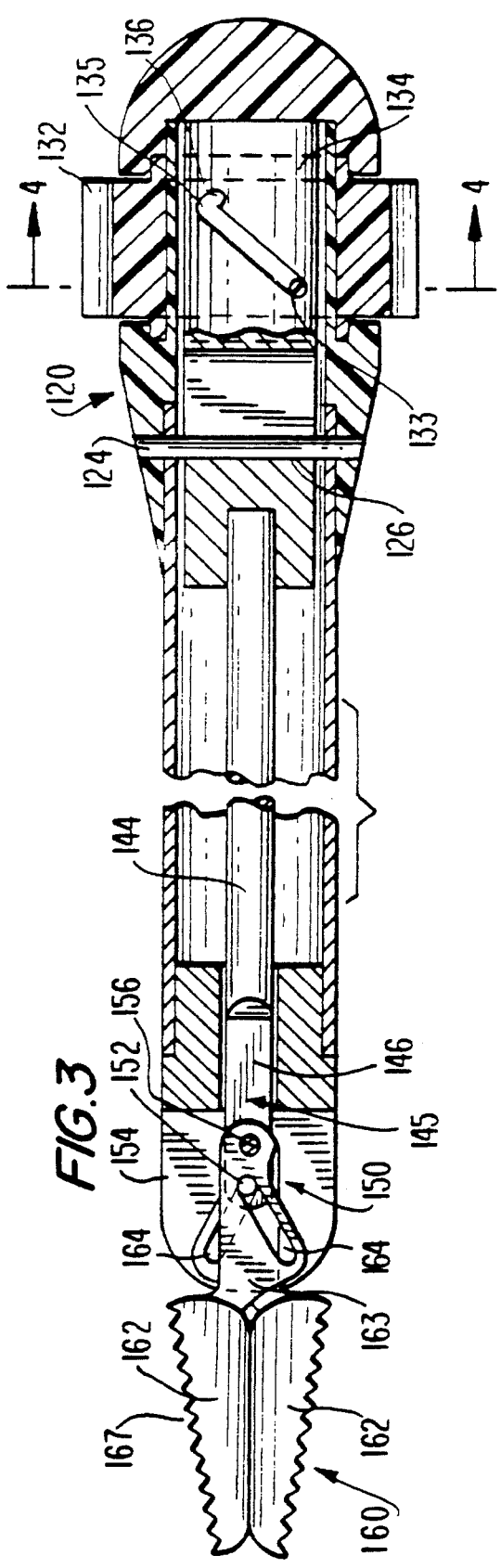

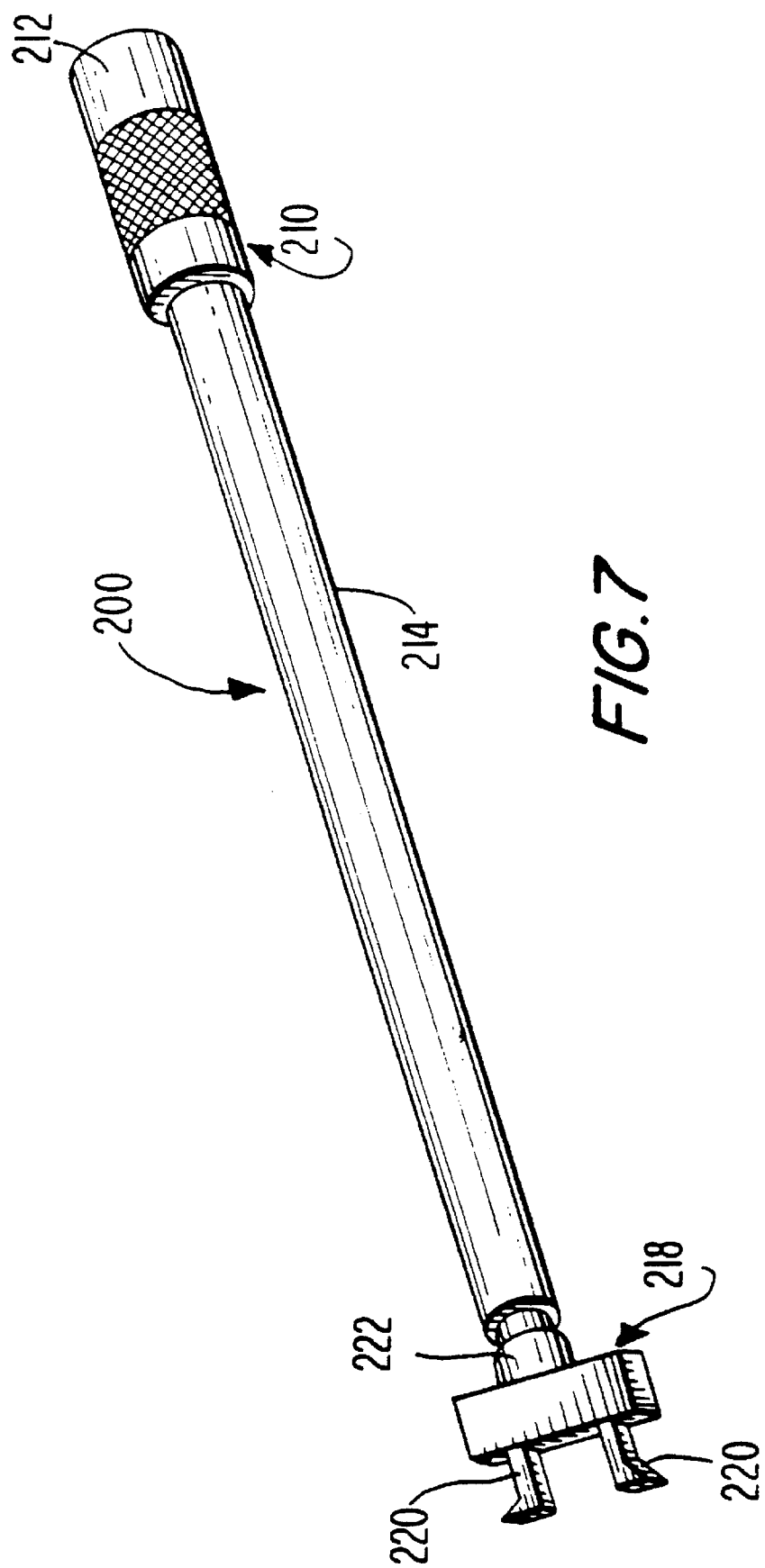

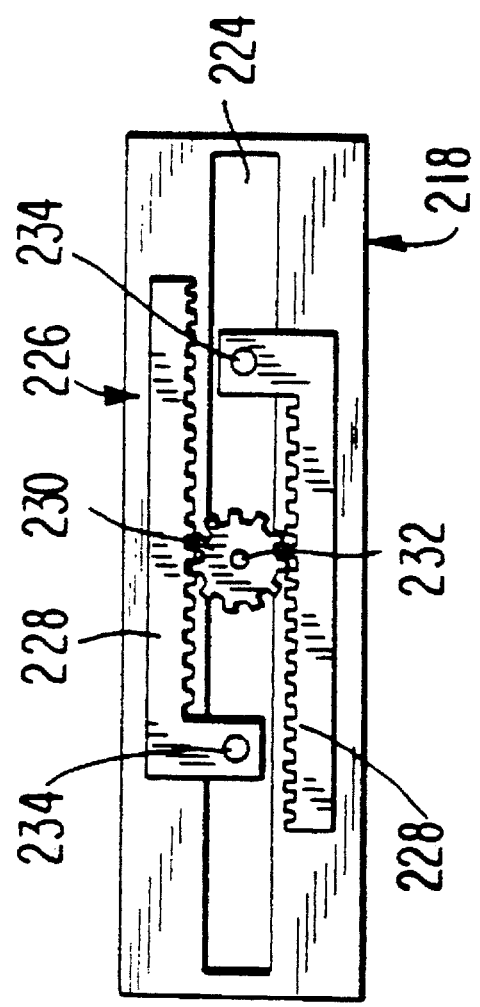

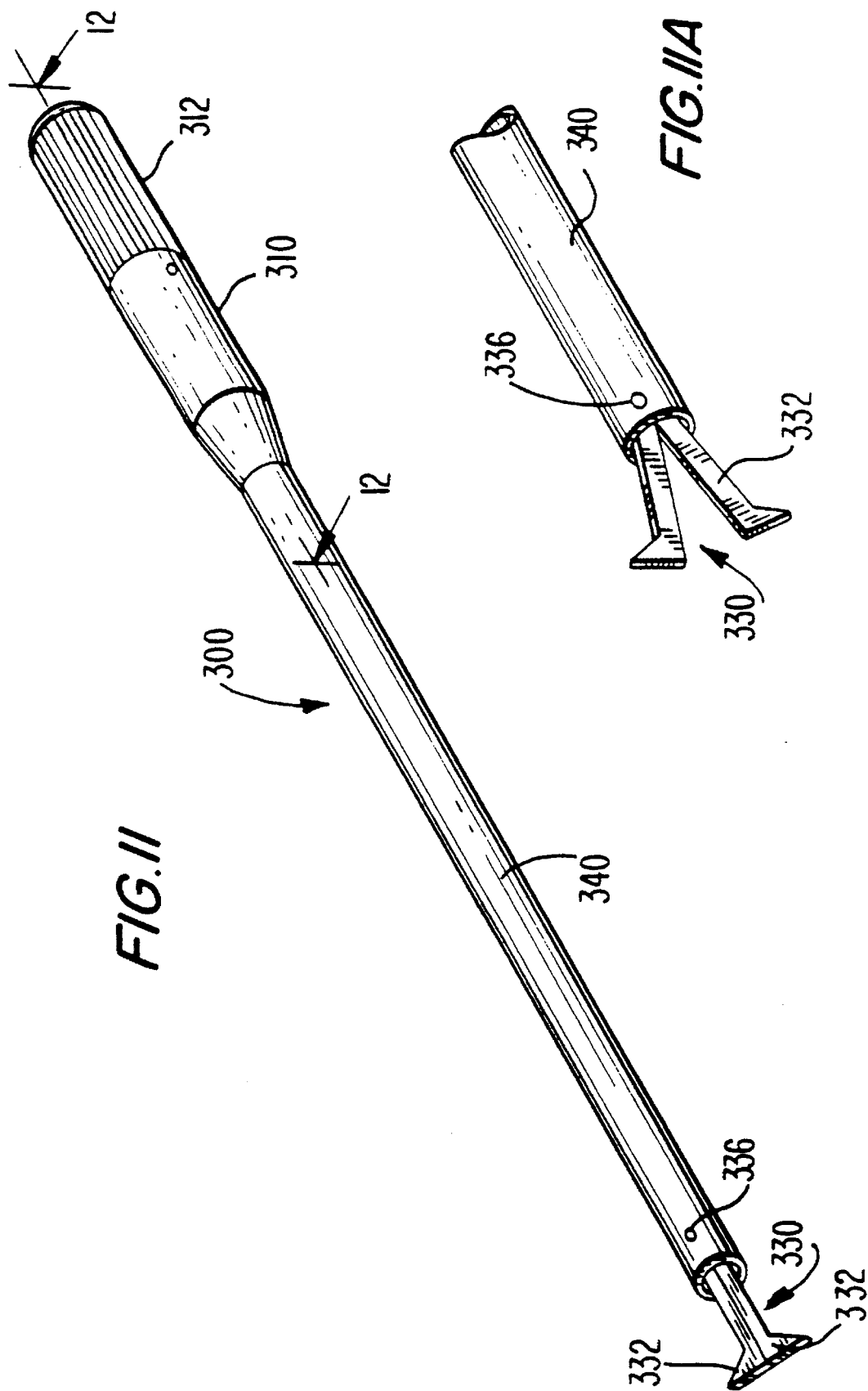

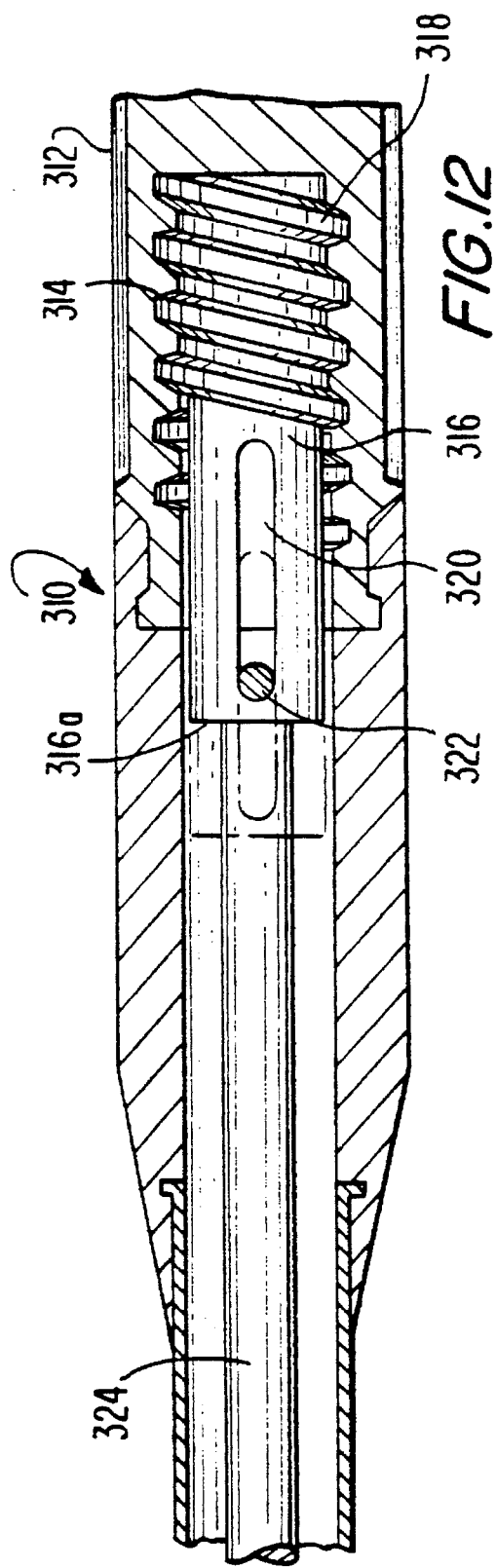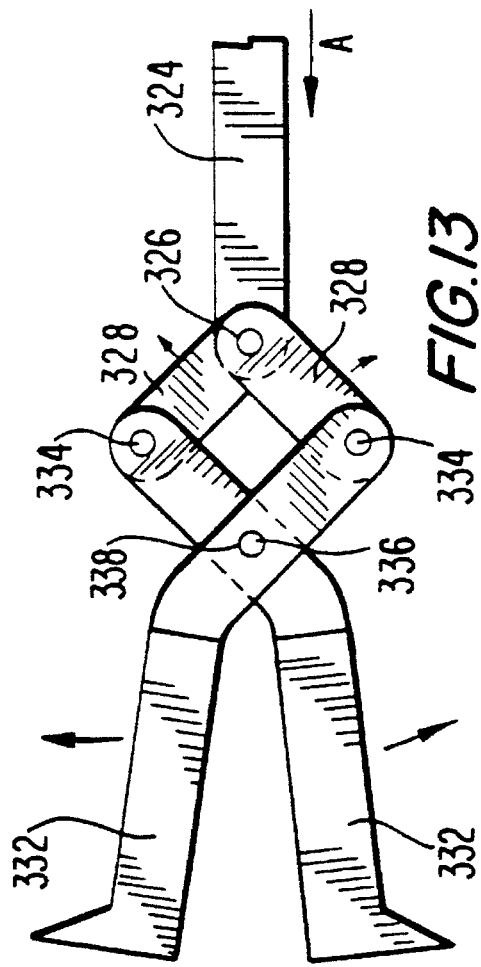

SURGICAL INSTRUMENTS AND METHOD USEFUL FOR ENDOSCOPIC SPINAL PROCEDURES

This is a continuation of application Ser. No. 08/214,875, filed on Mar. 16, 1994 now abandoned.

BACKGROUND OF THE INVENTION

1. Field of the Invention

The invention relates to surgical instruments and, more particularly, to endoscopic surgical instruments useful to perform endoscopic discectomy procedures and other minimally invasive spinal procedures.

2. Description of the Related Art

Back pain is a common affliction affecting millions of people. In many instances, back pain is caused by a herniated intervertebral disc. Intervertebral discs are generally cylindrical-shaped structures corresponding to the margins of the adjacent vertebrae. An outer ring known as the annulus fibrosus composed of concentric layers of fibrous tissue and fibrocartilage surrounds a cartilage-like core known as the nucleus pulposus. When an intervertebral disc is herniated, the softer nucleus projects through a torn portion of the annulus, creating a bulge which extends beyond the intervertebral foramen. As a result of the bulging disc, various spinal nerves may be compressed, causing pain or numbness.

Various procedures are used to treat herniated intervertebral discs. In mild disc herniation, pressure on adjacent nerves is lessened through non-surgical techniques. Such techniques include drugs (analgesics, anti-inflammatory drugs, muscle relaxants), physical therapy, and rest. If these non-surgical approaches are not successful, surgical intervention is necessary. Various surgical procedures have been developed to remove at least a portion of the herniated disc. Such procedures include laminotomies, laminectomies, and percutaneous discectomy.

In laminotomy (also referred to as interlaminar exploration), a posterior approach is used to access the spine through a longitudinal incision. Small amounts of the bony spinal lamina are removed, allowing access to, and removal of, portions of the herniated nucleus pulposus.

Laminectomy is a surgical procedure which, like laminotomy, uses a posterior approach to the herniated disc. In laminectomy, a larger portion of the spinal lamina or laminae are removed to access and remove portions of a herniated disc nucleus. Because both laminotomy and laminectomy require removal of bone and retraction of nerves and muscles, hospitalization and recuperation periods are lengthy. Additionally, removal of bone may lead to future spinal instability.

To minimize the need to remove portions of the vertebrae, other approaches to the herniated disc have been used. In particular, percutaneous discectomy employs a postero-lateral approach. Instruments are inserted through a cannula inserted through the patient's side. The disc annulus is pierced and the herniated nucleus is mechanically disintegrated, the pieces being removed through suction. This technique is shown for example in U.S. Pat. Nos. 4,545,374, 5,242,439 and Re 33,258.

Endoscopic surgery involves incising through body walls via small incisions, generally by use of a trocar having an obturator with sharp tip removably positioned in a cannula. After penetration, the obturator is removed leaving the cannula positioned in the body for reception of a camera or endoscope to transmit images to a remote TV monitor. Specialized instruments such as forceps, cutters, and applicators are inserted through other trocar sites for performing the surgical procedure while being viewed by the surgeon on the monitor. With the advent of endoscopic surgery and the recognition of its advantages over open procedures in reducing costs by shortening the patient's hospital stay and time of recovery so the patient can resume normal activity sooner, the industry has been viewing endoscopic discectomy as an alternative to the techniques and surgical methods described above. However, to date, the need exists for endoscopic instrumentation to properly and atraumatically improve access to the disc to facilitate removal for successful performance of endoscopic discectomy.

U.S. Pat. No. 5,195,541 discloses a laparoscopic surgical method for performing lumbar discectomy utilizing a single device. The single device is inserted into the patient anteriorly, the device comprising a sleeve having an endoscope receiving means, a laser fiber receiving means and a suction and irrigation channel means. This device, however, is of relatively large diameter because it must accommodate a variety of surgical instruments and therefore may obstruct the surgeon's view (on the TV monitor) and provide limited access to the disc.

There is a need in the art for surgical instrumentation which facilitates minimally invasive surgical techniques for anteriorly accessing the herniated disc. The instrumentation and techniques should advantageously improve access to the surgical site and permit the surgeon to endoscopically remove any desired amount of disc material With minimal interference to spinal nerves and adjacent back muscles. Such instrumentation and techniques would permit the surgical alleviation of back pain while providing the benefits attendant endoscopic/laparoscopic surgery, namely avoiding large incisions and long periods of hospital stay and patient recovery.

Such instrumentation could also advantageously be used for aiding other minimally invasive surgical spinal procedures such as spinal fusion.

SUMMARY OF THE INVENTION

The present invention provides a method for accessing at least a portion of an intervertebral disc for removal. The method comprises the steps of endoscopically accessing the invertebrae disc space through an anterior endoscopic port, inserting an endoscopic spreading instrument into the endoscopic port, spreading apart vertebrae adjacent to an intervertebral disc using the endoscopic spreading instrument, accessing an intervertebral disc nucleus, and removing at least a portion of the disc nucleus through the anterior endoscopic port.

The surgical method incorporating an anterior approach to access the intervertebral disc in combination with spreading of adjacent vertebrae permits the surgeon to have optimal viewing of the operation site as well as improves access to the site. Thus, the surgeon can accurately remove any desired amount of disc material to achieve the desired decompression of adjacent nerves and muscles.

The present invention also provides an endoscopic apparatus for spreading the vertebrae which includes a handle portion including an actuation member for manipulating an actuation mechanism, and an elongated endoscopic section defining a longitudinal axis and extending distally from the handle portion. The actuation mechanism at least partially extends within said elongated endoscopic section and movable in response to movement of the actuation member. A vertebrae spreading mechanism is operatively associated with a distal end of the endoscopic section and is movable between open and closed positions by the actuation mechanism in response to movement of the actuation member, the vertebrae spreading mechanism including at least two vertebrae spreading arm members having exterior vertebrae contacting surfaces. The vertebrae contacting surfaces may form an acute angle of elevation towards a proximal end of the instrument with respect to the longitudinal axis. The vertebrae spreading arms spread the vertebrae to assist endoscopic discectomy procedures as well as other minimally invasive spinal procedures such as spinal fusion.

BRIEF DESCRIPTION OF THE DRAWINGS

FIG. 1 is a perspective view of an endoscopic surgical instrument for spreading the vertebrae according to the present invention;

FIG. 1A is an enlarged perspective view of the distal end of the instrument of FIG. 1 with the vertebrae spreading arms in an open position;

FIG. 2 is a cross-sectional view of the instrument taken along lines 2—2 of FIG. 1;

FIG. 3 is a cross-sectional view of the instrument taken along lines 3—3 of FIG. 2;

FIG. 7 is a perspective view of an alternative embodiment adapted to spread vertebrae constructed according to the present invention;

FIG. 10 is a plan view of the double rack and pinion mechanism used to open and close the vertebrae spreading members of FIG. 7;

FIG. 11 is a perspective view of another alternative embodiment of an instrument adapted to spread vertebrae;

FIG. 11A is an enlarged perspective view of the distal end of the instrument of FIG. 11 with the vertebrae spreading arms in an open position;

FIG. 12 is a cross-sectional view of the handle of the instrument of FIG. 11 taken along the lines 12—12 of FIG. 11; and FIG. 13 is a plan view of the linkage mechanism for causing movement of the vertebrae spreading members of the instrument of FIG. 11.

DETAILED DESCRIPTION OF THE PREFERRED EMBODIMENT

A. Instrumentation

Figure 6:
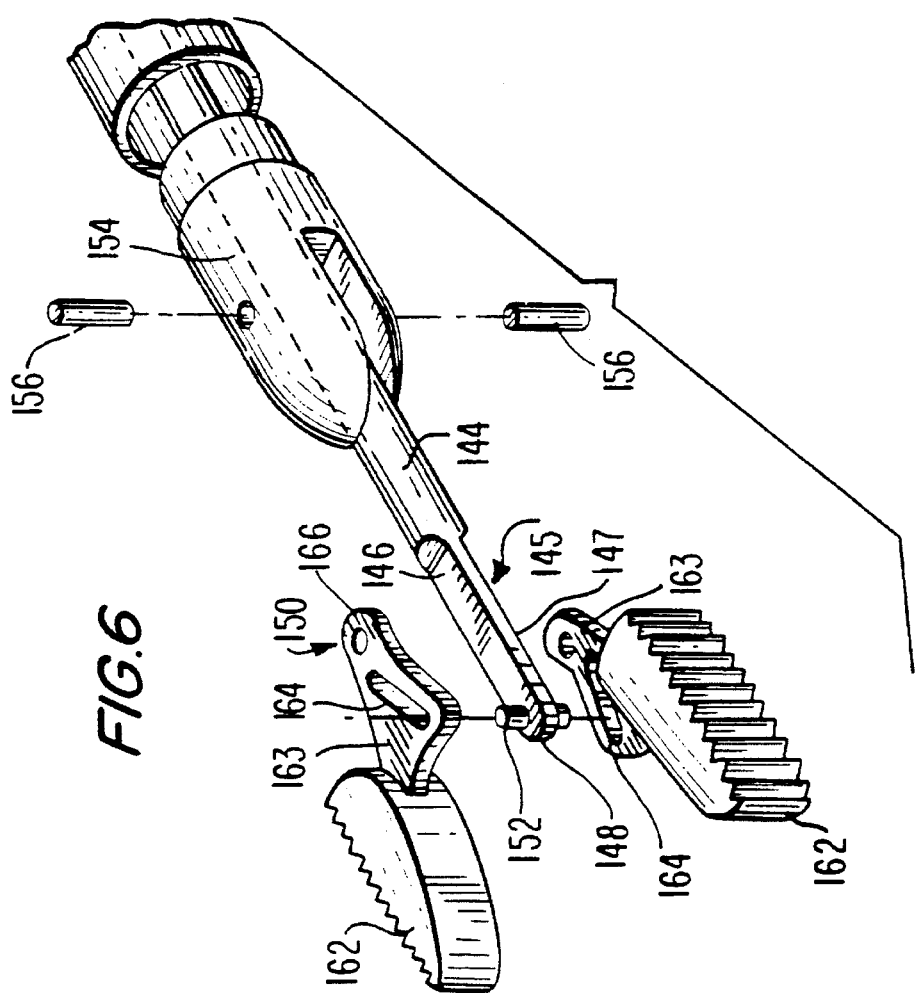
FIG. 6 is a perspective view with parts separated of the distal end of the instrument of FIG. 1.

Turning now to the drawings in detail in which like reference numerals identify similar or identical elements throughout the several views, FIG. 1 depicts an endoscopic surgical instrument 100 which may be used as a tissue spreader and particularly as a vertebrae spreader during an endoscopic discectomy procedure. By spreading the vertebrae, access to the disc is improved. In describing the surgical instruments of the present invention, the term "proximal" refers to a direction of the instrument away from the patient and towards the-user while the term "distal" refers to a direction of the instrument towards the patient and away from the user.

Surgical instrument 100 generally comprises proximal handle portion 110 having actuating member 132. Endoscopic portion 140 extends distally from handle portion 110 and is configured to support vertebrae spreading mechanism 160 at its distal end. Vertebrae spreading mechanism 160 includes a pair of serrated vertebrae spreading arms 162 shown in a closed position in FIG. 1 and in an open position in FIG. 1A.

Figure 4:
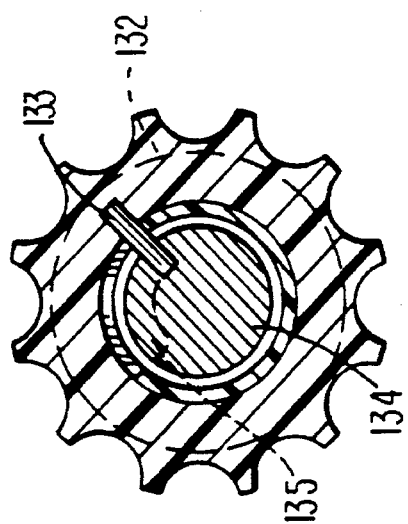
FIG. 4 is a cross-sectional view of the instrument taken along lines 4—4 of FIG. 3.

Referring now to FIGS. 2 and 3, in conjunction with the axial cross-sectional view of FIG. 4, the actuating mechanism 130 comprises a rotatable collar actuating member 132 and translatable inner cylindrical member 134. Translatable inner cylindrical member 134 is provided with angled camming slot 135 for cooperating with cylindrical camming pin 133. Camming pin 133, mounted to rotatable actuating member 132, travels within camming slot 135 during rotation of member 132 to axially translate cylindrical member 134 within handle portion 120 and proximal end portion of endoscopic portion 140. To ensure longitudinal reciprocal motion of the cylindrical member 134, guide pin 124 is mounted through handle portion 120 into cylindrical member longitudinal guide slots 126. Cam slot 135 includes angled portion 136 to lock the camming pin 133 when the arms 162 are in the open position.

Referring now to FIGS. 2 and 3, in conjunction with FIG. 6, mounted within the distal end of the cylindrical member 134 is actuating rod 144. Actuating rod 144 passes coaxially through endoscopic portion 140 to move vertebrae spreading mechanism 160 between open and closed positions. A separate seal, such as O-ring 143 can be provided to prevent passage of gases from the body cavity. At its distal end, actuating rod 144 terminates in flattened portion 145 having flat surfaces 146 and 147. To link vertebrae spreading mechanism 160 to actuating rod 144, linkage mechanism 150 is provided, as shown in FIG. 6. A transverse bearing post 152 which interfits with vertebrae spreading arms 162 is attached to actuating rod 144 through aperture 148. Linkage mechanism 150 is contained within linkage mechanism housing 154, a hollow member supported at the distal end of endoscopic portion 140 through an interference fit.

Figure 5:
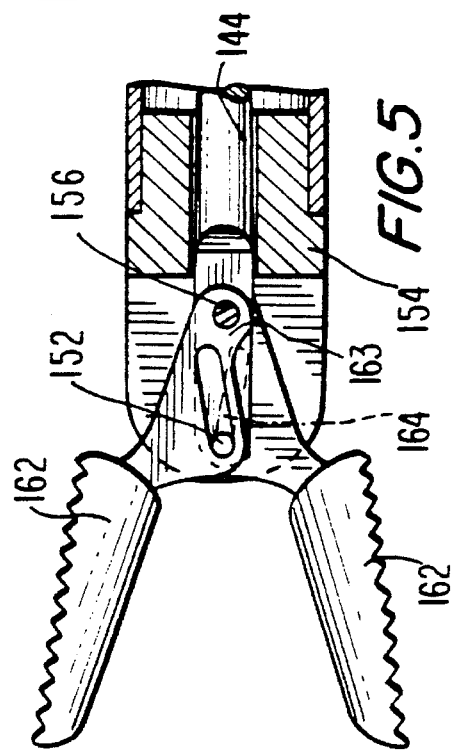
FIG. 5 is a cross-sectional view illustrating the vertebrae spreading portion of the instrument taken along lines 5—5 of FIG. 1A.

Each of vertebrae spreading members 162 has a proximally-extending planar arm portion 163 mounted within linkage mechanism housing 154. Planar arm portions 163 are each provided with an angled camming slot 164 to permit movement of the vertebrae spreading members between open and closed positions. Vertebrae spreading members 162 include proximal transverse circular apertures 166 configured to receive transverse pivot pins 156 mounted through linkage mechanism housing 154. Bearing post 152 interfits within angled camming slots 164 to translate the longitudinal reciprocal motion of actuating rod 144 into pivotal motion of vertebrae spreading members 164 about transverse pivot pins 156. FIG. 5 illustrates actuator rod 144 fully extended to thereby move vertebrae spreading members 162 to the fully opened position. Tissue gripping surface 167 formed on an outer surface of arms 162 preferably includes a plurality of teeth to prevent slippage of gripping surface 167 on tissue when spreading members 162 are open.

As best seen in FIG. 3, the tissue gripping surface 167 of each of the vertebrae spreading arms 162 forms an acute angle of elevation, T, with the longitudinal axis defined by endoscopic portion 140, towards the proximal end of instrument 100. This configuration aids in spreading the vertebrae since the distalmost portion of the vertebrae spreading arms are narrower than the proximalmost portion, enabling insertion of the instrument within confined spaces, such as, between adjacent vertebrae. Each of the vertebrae spreading arms are composed of rigid material such as stainless steel or rigid polymer.

Referring now to FIG. 7 there is illustrated an alternative embodiment of an instrument useful as a vertebrae spreader constructed according to the invention. Instrument 200 includes handle portion 210 having actuating knob 212 and elongated member 214 extending distally form the handle portion 210. Supported at the distal end of elongated member 214 is vertebrae spreading housing member 218 which houses vertebrae spreading members 220.

Handle portion 210 and connected elongated member 214 may be similar to a conventional allen wrench, appropriately reconfigured and dimensioned to be received within a trocar or cannula. The distal end of elongated (endoscopic) member 214 (not shown) preferably defines a generally hexagonal shape in cross section which is received within a correspondingly dimensioned hexagonal-shaped recess formed in inlet portion 222 of housing member 218 to releasably connect the elongated member to the housing member. Inlet portion 222 rotates in response to rotational movement of handle portion 210 and elongated member 214, the significance of which will become appreciated from the description provided below. This releasable connection of elongated member 214 to inlet portion 222 allows the vertebrae spreading arms to be positioned and left in the body during the remainder of the operation, while the elongated member 214 is removed to free the port (trocar site) for insertion of other instrumentation. At any time during the procedure, elongated member 214 can be reinserted into the body and re-connected to inlet portion 222 and vertebrae spreading arms 220 to move the arms to the closed position (FIG. 8) for withdrawal from the body.

Figure 9:
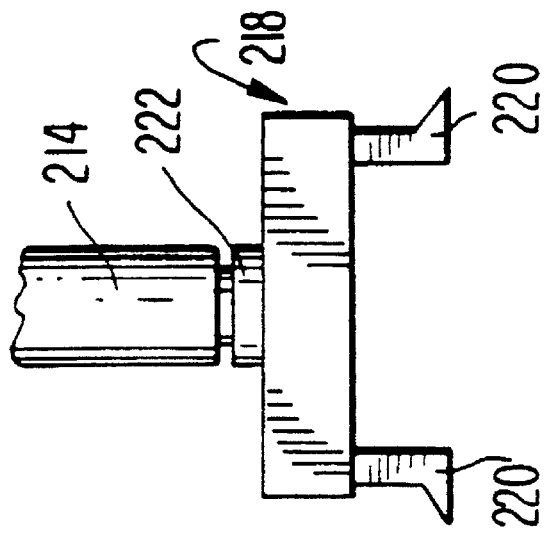
FIG. 9 is a view similar to the plan view of FIG. 8 depicting the vertebrae spreading members in an open position.
Figure 8:
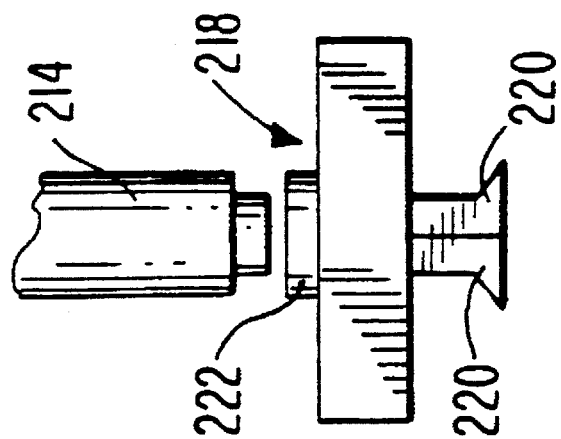
FIG. 8 is a side plan view of the distal end portion of the instrument of FIG. 7 illustrating the vertebrae spreading members in a generally closed position.

Referring now more specifically to FIGS. 8–10, in conjunction with FIG. 7, housing member 218 houses vertebrae spreading members 220 which are adapted for reciprocal sliding movement within channel 224 formed in the housing. Vertebrae spreading members 220 move to and from the center of housing member 218 through actuation of a double rack and pinion system 226 as depicted in FIG. 10. Double rack and pinion system 226 includes racks 228 and pinion 230. Racks 228 intermesh with pinion 230 and move to and from the center of housing member 218 in response to rotational movement of pinion 230. Pinion 230 is operatively connected to inlet portion 222 of housing member 218 through pin 232, and rotates with the inlet portion.

Each vertebrae spreading member 220 is operatively connected to a single rack 228 by connecting pins 234 (see FIG. 10) and, accordingly, moves either inwardly or outwardly relative to the center of housing member 218 in response to corresponding movement of the rack. Thus, rotation of handle portion 210 and elongated member 214 in the clockwise direction causes corresponding clockwise motion of pinion 230 which, accordingly, positions vertebrae spreading members adjacent each other as illustrated in FIG. 8. Consequently, counter clockwise rotation of pinion 230 (FIG. 10) positions spreading members 220 in the outward open condition depicted in FIG. 9. It should be noted that the movement of arms 220 is transverse to the longitudinal axis of the instrument and arm 220 remain substantially parallel (e.g. in parallel planes) to the longitudinal axis during movement between the open and closed positions.

Referring now to FIGS. 11–13, there is illustrated another embodiment of a surgical instrument useful as a vertebrae spreader, constructed according to the present invention. Vertebrae spreader 300 includes a handle portion 310 having an actuating member 312 at a proximal end and an elongated, substantially cylindrical endoscopic portion 340 extending distally from the handle portion. A vertebrae spreading mechanism 330 is supported at the distal end of endoscopic portion 340. Spreading mechanism 330 includes a pair of vertebrae spreading members 332, shown in a deployed position in FIG. 11A, useful for spreading vertebrae during an endoscopic discectomy procedure.

As shown in FIG. 12, handle portion 310 includes rotatable actuating knob member 312 provided with a threaded axial interior bore 314. Threaded bore 314 engages a threaded driving member 316 having an elongated threaded body portion 318. Lateral longitudinal slots 320 in driving member 316 cooperate with through pin 322 to permit axial translation of threaded driving member 316 during rotational movement of knob member 312 while prohibiting rotational movement of the driving member.

A rod member 324 is connected to the distal end portion 316a of driving member 316 by conventional means. Rod member 324 moves axially in direct response to corresponding axial movement of driving member 316.

Referring now to FIG. 13, the distal end of rod member 324 is connected via pin 326 to a pair of link members 328. Link members 328 are connected to respective vertebrae spreading members 332 via connecting pins 334. A transverse pin 336 is positioned within an aperture 338 formed in each vertebrae spreading member. Pin 336 traverses the longitudinal bore of endoscopic portion 340 and is securely mounted to the endoscopic portion 340 by conventional means (FIG. 11).

In use of instrument 300, rotation of actuating member 312 produces axial translation of driving member 316 and rod member 324. During distal movement of rod member 324 (as shown by the arrow A in FIG. 13), link members 328 move outwardly, in the direction shown by the directional arrows, which outward movement causes vertebrae spreading members 332 to pivot about pin 336 to an open position. Proximal movement of rod member 324 causes inward movement of link members 328 and corresponding inward pivoting movement of vertebrae spreading members 332 to a closed condition.

As noted above, FIGS. 1–13 illustrate vertebrae spreaders useful for spreading apart adjacent vertebrae during endoscopic discectomy procedures. However, these instruments can also be utilized in other surgical procedures and for spreading other types of tissue besides bone.

The instruments described above are preferably composed of relatively inexpensive materials so that they are single-use disposable instruments which can be discarded after use. However, it is also contemplated that they can be re-usable or semi-reusable in that a portion of the instrument is re-sterilized, e.g. the handle, and the remaining portion is disposable, e.g. the jaw structure.

B. Surgical Method

Use of the surgical instruments of FIGS. 1–13 will be described in conjunction with an anterior endoscopic lumbar discectomy according to the present invention. While they have particular application in this procedure, it is recognized that the instruments of the present invention may be used to perform surgical spreading procedures anywhere in the body. In describing the procedure, the term "anterior" is broadly used to describe the ventral surface of a body opposite the back. This term includes, but is not limited to, the abdominal region of the body.

For performing an anterior endoscopic lumbar discectomy, the patient is placed in the supine position and entry is made through the abdomen, which is insufflated according to known procedures. Specific points of entry are determined by the particular intervertebral disc to be removed. For removal of intervertebral discs of the lumbar vertebrae, ports are established in the lower abdomen using standard trocars. One port is dedicated to viewing via an endoscope, while remaining ports are used for surgical instrument insertion and manipulation.

To access the intervertebral disc, soft tissue is dissected, providing a pathway through the abdominal region. Fascia and other soft tissue may be spread using a surgical retractor or tissue spreader. Organs such as the colon are retracted away from the operating site to increase exposure and facilitate observation of the spinal column.

Upon reaching the spinal column, blunt dissection is performed to expose the intervertebral disc. Fascia is removed from the disc area and spread using a retractor or instrument for spreading tissue.

To further facilitate access to the intervertebral disc, the adjacent vertebrae are spread using any one of the instruments of the present invention. The distal end of the selected instrument is placed between the vertebral bodies. Deployment of the vertebrae spreader causes the arms to expand against each adjacent vertebral body, relieving pressure of the vertebrae on the disc and improving access to ease disc removal.

The herniated disc nucleus is accessed through the disc annulus. The disc annulus may be incised using a conventional endoscopic cutting instrument. Such instruments include for example endoscopic scissors. A portion of the disc annulus may be removed to form an access channel, or, an incision may be created and the incision edges spread open through the tissue spreading element. Alternatively, the disc annulus may be incised using a laser or an access port created using a trephine.

The cutting instrument is inserted into the disc nucleus. Following insertion into the disc nucleus, the cutting instrument slices away portions of the disc nucleus which may be removed using forceps, rongeurs, or suction instruments. Other instruments may be selected for disc removal including lasers, rongeurs, and the like. Using the anterior approach, as much or as little of the herniated nucleus may be removed as needed to alleviate compression of adjacent muscles and nerves. This surgical procedure permits the surgeon to directly monitor the disc removal process by means of an endoscope.

Although the use of the instrumentation of the present invention has been described in conjunction with endoscopic discectomy procedures, the instruments can be used for facilitating other endoscopic (minimally invasive) surgical procedures. These include, for example, spreading the vertebrae to aid spinal fusion. Spinal fusion is used to stabilize spinal segments and is currently performed using fusion baskets, bone plugs or other internal fixation devices.

While the invention has been particularly shown and described with reference to the preferred embodiments, it will be understood by those skilled in the art that various modifications and changes in form and detail may be made without departing from the scope and spirit of the invention. Accordingly, modifications such as those suggested above, but not limited thereto, are to be considered within the scope of the invention.

What is claimed is:

1. A method for accessing vertebral structures comprising:

forming an endoscopic channel on an anterior portion of a patient's body;

inserting an endoscopic vertebrae spreading instrument into said endoscopic channel; and spreading adjacent vertebrae in the spinal column using said endoscopic vertebrae spreading instrument.

2. A method for intervertebral disc removal comprising: endoscopically accessing the spinal column through an anterior endoscopic port;

inserting an endoscopic spreading instrument into the endoscopic port:

spreading apart vertebrae adjacent an intervertebral disc using the endoscopic spreading instrument;

accessing an intervertebral disc nucleus; and removing at least a portion of the disc nucleus through said anterior endoscopic port.

3. A method for intervertebral disc removal according to claim 2 wherein the step of accessing an intervertebral disc nucleus includes removal of a portion of an intervertebral disc annulus.

4. A method for intervertebral disc removal according to claim 2 further comprising the step of cutting the disc nucleus with an endoscopic cutting instrument prior to the step of removing at least a portion of said disc nucleus through said anterior endoscopic port.

5. The method for intervertebral disc removal according to claim 2, wherein the step of spreading apart vertebrae includes positioning at least two vertebrae spreading arm members of said endoscopic spreading instrument between adjacent vertebrae and moving said arm members to an open position to spread the vertebrae.

6. The method for intervertebral disc removal according to claim 5, wherein the step of spreading apart vertebrae includes initially positioning said arm members of said endoscopic spreading instrument between the vertebrae such that exterior tissue contacting surfaces contact the vertebrae and thereafter moving said arm members to said open position to spread the vertebrae.

7. The method for intervertebral disc removal according to claim 6, wherein the step of spreading apart vertebrae includes pivoting said arm members from a closed position to said open position.

8. The method for intervertebral disc removal according to claim 5, wherein the step of spreading apart vertebrae includes actuating an actuating mechanism of said endoscopic spreading instrument to move said arm members to said open position thereof.

9. The method for intervertebral disc removal according to claim 8, wherein the step of actuating the actuating mechanism includes rotating a rotatable control knob of said actuating mechanism to move said arm members to said open position.

10. The method for intervertebral disc removal according to claim 5, wherein the step of spreading apart vertebrae includes initially positioning said arm members between adjacent vertebrae such that said arm members are in general parallel relation with a longitudinal axis defined by said endoscopic spreading instrument and thereafter moving said arm members in an opposed direction to said open position to spread the vertebrae.

11. The method for intervertebral disc removal according to claim 10, wherein the step of spreading apart vertebrae includes moving said arm members in the transverse direction to said open position while maintaining the parallel relation of said arm members with said longitudinal axis.

12. The method for intervertebral disc removal according to claim 8 wherein the step of actuating the actuating mechanism reciprocates an actuating rod interfitting with one of said arm members.

* * * * *